United States Patent
Moore et al.

(10) Patent No.: US 6,457,860 B1
(45) Date of Patent: Oct. 1, 2002

(54) LIGHT-WEIGHT IMAGING ASSEMBLIES FOR ONCOLOGY PORTAL IMAGING

(75) Inventors: William E. Moore, Macedon; David J. Steklenski, Rochester, both of NY (US)

(73) Assignee: Eastman Kodak Company, Rochester, NY (US)

( * ) Notice: Subject to any disclaimer, the term of this patent is extended or adjusted under 35 U.S.C. 154(b) by 9 days.

(21) Appl. No.: 09/757,868

(22) Filed: Jan. 10, 2001

(51) Int. Cl.$^7$ ................................................ A61B 6/08
(52) U.S. Cl. ........................ 378/205; 378/182; 378/185
(58) Field of Search ............................ 378/265, 182, 378/185; 430/139, 966

(56) References Cited

U.S. PATENT DOCUMENTS 5,712,486 A * 1/1998 Soltani et al. ........... 250/484.4
5,871,892 A   2/1999 Dickerson et al.

OTHER PUBLICATIONS

Hammoudah MM. & Henschke, "Supervoltage Beam Films", International J. of Radiation Oncology, Biology, Physics, vol. 2, pp. 571–577, 1977.

D.A. Jaffray, JJ Battista, A. Fenster & PBE Munroe, X–ray Scatter in Megavoltage Transission Radiography: Physical Characteristics and Influence on Image Quality, vol. 21, pp. 45–60, 1994.

R.T. Droege & B.E. Bjarngard, J. Medical Physics, "Metal Screen Film Detector MTF at Megavoltage X–ray Energies", vol. 6, pp. 515–518, 1979.

R.T. Droege & B.E. Bjarngard, J. Medical Physics, "Influence of Metal Screens on Contrast in Megavoltage X–ray Imaging"1 vol. 6, pp. 487–493, 1979.

B.A. Groh, L. Spies, B.M. Hess–& T. Bortfeld, "Scatter rejection methods in megavoltage imaging with an amorphous silicon flat panel array", SPIE, vol. 3977, 2000.

W.E. Moore & D.J. Steklenski, "Radiation Oncology Portal Imaging", US 09/651,761 filed Aug. 31, 2000.

W–L A. Chen, A.P. Chipouras, T.A. Heath, W.A. Mruk, D.J. Steklenski, "Image Storage Phosphor Panels Having Flexible Supports", US 09/668,150 filed Sep. 21, 2000.

* cited by examiner

*Primary Examiner*—David P. Porta
*Assistant Examiner*—Elizabeth Gemmell
(74) *Attorney, Agent, or Firm*—J. Lanny Tucker (57) ABSTRACT

Imaging assemblies comprise thin metal screens adjacent fluorescent intensifying screens. Such assemblies can be included as part of radiographic imaging assemblies in which a radiographic film is positioned behind the metal and fluorescent intensifying screens. The metal screen is from about 0.01 to about 0.75 mm in thickness when composed of copper and from about 0.05 to about 0.40 mm when composed of lead. Photospeed and other imaging characteristics are not diminished with the use of these relatively thin metal screens.

19 Claims, 2 Drawing Sheets

LIGHT-WEIGHT IMAGING ASSEMBLIES FOR ONCOLOGY PORTAL IMAGING

FIELD OF THE INVENTION

This invention is directed to radiography and in particular to imaging assemblies (or "cassettes") and radiographic imaging assemblies that are useful for oncology portal imaging. Thus, this invention is useful in portal radiography.

BACKGROUND OF THE INVENTION

In conventional medical diagnostic imaging the object is to obtain an image of a patient's internal anatomy with as little X-radiation exposure as possible. The fastest imaging speeds are realized by mounting a dual-coated radiographic element between a pair of fluorescent intensifying screens for imagewise exposure. About 5% or less of the exposing X-radiation passing through the patient is adsorbed directly by the latent image forming silver halide emulsion layers within the dual-coated radiographic element. Most of the X-radiation that participates in image formation is absorbed by phosphor particles within the fluorescent screens. This stimulates light emission that is more readily absorbed by the silver halide emulsion layers of the radiographic element.

Examples of radiographic element constructions for medical diagnostic purposes are provided by U.S. Pat. No. 4,425,425 (Abbott et al.) and U.S. Pat. No. 4,425,426 (Abbott et al.), U.S. Pat. No. 4,414,310 (Dickerson), U.S. Pat. No. 4,803,150 (Kelly et al.) and U.S. Pat. No. 4,900,652 (Kelly et al.), U.S. Pat. No. 5,252,442 (Tsaur et al.), and *Research Disclosure,* Vol. 184, August 1979, Item 18431.

Radiation oncology is a field of radiology relating to the treatment of cancers using high energy X-radiation. This treatment is also known as teletherapy, using powerful, high energy X-radiation machines (often linear accelerators) or cobalt (60) units to exposure the cancerous tissues (tumor). The goal of such treatment is to cure the patient by selectively killing the cancer while minimizing damage to surrounding healthy tissues.

Such treatment is commonly carried out using high energy X-radiation, 4 to 25 MVp. The X-radiation beams are very carefully mapped for intensity and energy. The patient is carefully imaged using a conventional diagnostic X-radiation unit, a CT scanner, and/or an MRI scanner to accurately locate the various tissues (healthy and cancerous) in the patient. With full knowledge of the treatment beam and the patient's anatomy, a dosimetrist determines where and for how long the treatment X-radiation will be directed, and predicts the radiation dose to the patient.

Usually, this causes some healthy tissues to be overexposed. To reduce this effect, the dosimetrist provides one or more custom-designed "blocks" or shields of lead around the patient's body to absorb X-radiation that would impact healthy tissues.

To determine and document that a treatment radiation beam is accurately aimed and is effectively killing the cancerous tissues, two types of imaging are carried out during the course of the treatment. "Portal radiography" is generally the term used to describe such imaging. The first type of portal imaging is known as "localization" imaging in which the portal radiographic film is briefly exposed to the X-radiation passing through the patient with the lead shields removed and then with the lead shields in place. Exposure without the lead shields provides a faint image of anatomical features that can be used as orientation references near the targeted feature while the exposure with the lead shields superimposes a second image of the port area. This process insures that the lead shields are in the correct location relative to the patient's healthy tissues. Both exposures are made using a fraction of the total treatment dose, usually 1 to 4 monitor units out of a total dose of 45–150 monitor units. Thus, the patient receives less than 20 RAD's of radiation.

If the patient and lead shields are accurately positioned relative to each other, the therapy treatment is carried out using a killing dose of X-radiation administered through the port. The patient typically receives from 50 to 300 RAD's during this treatment. Since any movement of the patient during exposure can reduce treatment effectiveness, it is important to minimize the time required to process the imaged films.

A second, less common form of portal radiography is known as "verification" imaging to verify the location of the cell-killing exposure. The purpose of this imaging is to record enough anatomical information to confirm that the cell-killing exposure was properly aligned with the targeted tissue. The imaging film/cassette assembly is kept in place behind the patient for the full duration of the treatment. Verification films have only a single field (the lead shields are in place) and are generally imaged at intervals during the treatment regime that may last for weeks. Thus, it is important to insure that proper targeted tissue and only that tissue is exposed to the high level radiation because the levels of radiation are borderline lethal.

Portal radiographic imaging film, assembly and methods are described, for example, in U.S. Pat. No. 5,871,892 (Dickerson et al.) in which the same type of radiographic element can be used for both localization and portal imaging.

Some of the earliest portal radiation images were recorded on "direct" radiographic films that were designed for industrial purposes. These films were often placed in cardboard film holders and required special processing techniques. However, such imaging "assemblies" had the advantage of being lightweight and easy to carry. To address this problem, Eastman Kodak Company introduced films in the early 1970's in light-tight envelopes and ready for use in portal and localization imaging. These films could be used without a film holder or cassette and were even more lightweight and convenient to use because they could be processed using conventional techniques and equipment. However, the images obtained at higher energies were poor in quality.

As high energy linear accelerators became more commonly used, it was determined by several researchers in the field that metal plates should be used during portal imaging (see for example, Hammoudah et al., *Int.J Radiation Oncol. Biol. Phys.* 2, 571–577, 1977 and Droege et al., *Medical Physics,* 6, pp. 487–493 and pp. 515–518, 1979). Consequently, several years later, several manufacturers introduced imaging assemblies ("cassettes") for portal and localization imaging that included either or both front and back metal plates. These imaging assemblies provided improved images at higher treatment energies, but because of the inclusion of the one or more metal plates, they were much heavier and difficult to handle and transport throughout the medical community.

Even with the inclusion of the heavier metal plate, the final image contrast was observed to be too low. Current imaging assemblies commercially available include a 1 mm copper front metal screen, front and back gadolinium oxysulfide fluorescent intensifying screens and a back lead metal screen. These imaging assemblies also include a high contrast fine grain silver halide radiographic film to provide much improved portal images. However, the weight of such imaging assemblies is considerable and creates a problem for users in the medical imaging community.

Since the earliest teaching about the need for metal screens in the imaging assemblies, the thickness of the metal screens has been set at 1 mm or more. It was consistently believed that thick metal screens were required to avoid overexposure especially for portal imaging. Thus, commercial products have consistently included at least 1 mm-thick metal screens in the front of the imaging assembly.

Presently, in portal imaging, the multi-$MV_p$ X-radiation in part passes through the patient unabsorbed and is in part absorbed creating a secondary electron emission. The front metal screen is usually relied upon to intercept and absorb the secondary electron emission. This lowers minimum density and significantly enhances image sharpness. Image intensification (raising maximum density and contrast) is achieved by absorbing X-radiation and transmitting to the radiographic film the electrons that are thereby generated.

Figure 1:
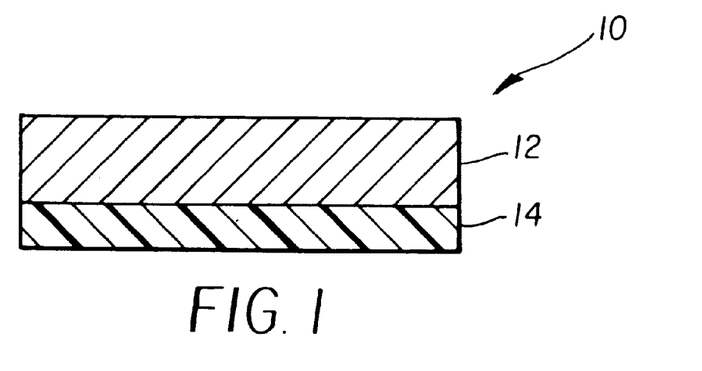
FIG. 1 is an enlarged cross sectional view of a conventional portal imaging assembly for direct exposure.

In addition to the front metal screen, which is always present, a back metal screen can also be employed to provide an additional source of electrons for radiographic film exposure. Conventional portal imaging assemblies can be grouped into two categories. In the first category, the imaging assembly includes one or two metal plates and a photographic silver halide film that is designed for direct exposure to X-rays or electrons. Two such films are commercially available from Eastman Kodak Company as KODAK X-RAY Therapy Localization (XTL) Film and KODAK X-RAY Verification (XV) Film. Such direct X-ray exposure assemblies are illustrated in FIG. 1 (described in more detail below). A commercial imaging assembly of this type is commercially available as KODAK EC-L Cassette from Eastman Kodak Company.

Figure 2:
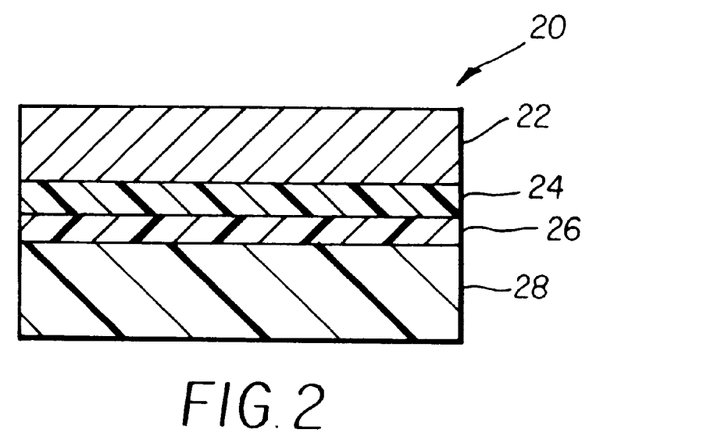
FIG. 2 is an enlarged cross sectional view of a conventional portal imaging assembly using fluorescent intensifying screens (indirect exposure).

The second portal imaging assembly uses a radiographic photographic silver halide film containing fine grain silver halide emulsions, one or two fluorescent (or phosphor) screens (or intensifying panels) and one or two metal plates. One such assembly is illustrated in FIG. 2 (described in more detail below). Although the assembly in FIG. 2 shows only one metal plate, other assemblies can have both front and back metal plates. A commercial imaging assembly of this type is KODAK EC-L.

Both portal imaging assemblies provide the desired high contrast images, but because of the thick metal screens used to provide the desired imaging features, they are very heavy and difficult and unsafe to carry throughout medical facilities. Medical users have tolerated this disadvantage because it has been believed that the thick metal plates are necessary for desired imaging properties.

We have found that this is not the case and it is to this problem that the present invention is directed.

SUMMARY OF THE INVENTION

The present invention provides an imaging assembly comprising a metal intensifying screen that is positioned adjacent to a fluorescent intensifying screen, the metal intensifying screen having a thickness of from about 0.1 to 0.75 mm when composed of copper or a thickness of from about 0.05 to 0.40 mm when composed of lead.

The present invention also provides a radiographic imaging assembly comprising a dual emulsion-coated radiographic silver halide film provided in combination with a metal intensifying screen that is positioned adjacent to the frontside of the radiographic film, and a fluorescent intensifying screen that is interposed between the radiographic silver halide film and the metal intensifying screen, the metal intensifying screen having a thickness of from about 0.1 to 0.75 mm when composed of copper or a thickness of from about 0.05 to 0.40 mm when composed of lead.

Still again, this invention provides a method of confirming the targeting of X-radiation comprising:

A) positioning the radiographic imaging assembly described above to a region of a subject, B) directing the X-radiation at the region of the subject containing features that are identifiable by differing levels of X-radiation absorption and creating a first image of X-radiation penetrating the subject with the radiographic film as part of the radiographic imaging assembly described above, C) directing X-radiation at the region of the subject and creating a second image superimposed on the first image in the radiographic film, D) processing the radiographic film to obtain a viewable image from which intended targeting of the X-radiation directed at the region in relation to identifiable features of the subject is realized, wherein during steps A and B, total X-radiation exposure is limited to 10 seconds or less.

The present invention provides a means for portal imaging using a light weight imaging assembly (or cassette) that has the desired imaging properties. It was a surprise to us that the thickness of at least the front metal intensifying screen could be significantly reduced from 1 mm without any significant loss in imaging properties or photographic speed. This invention will allow users to achieve portal imaging with lightweight portal imaging systems that are safer and easier to handle.

DETAILED DESCRIPTION OF THE INVENTION

Definition of Terms

The term "positioned adjacent" is used to define the positional relationship of the metal intensifying screen and the fluorescent intensifying screen in the imaging assemblies of this invention. It refers to both screens being in intimate contact as well as the screens being separated by a gap of up to 3 mm. Such a gap can be created by an adhesive layer, air, or a compressible porous material.

The term "contrast" as herein employed indicates the average contrast derived from a characteristic curve of a radiographic element using as a first reference point (1) a density ($D_1$) of 0.25 above minimum density and as a second reference point (2) a density ($D_2$) of 2.0 above minimum density, where contrast is $\Delta D$ (i.e. 1.75)÷$\Delta$ $\log_{10}$ E($\log_{10}$ $E_2$–$\log_{10}$ $E_1$), $E_1$ and $E_2$ being the exposure levels at the reference points (1) and (2).

"Gamma" is described as the instantaneous rate of change of a D log E sensitometric curve or the instantaneous contrast at any log E value.

"Peak gamma" is the point of the sensitometric curve where the maximum gamma is achieved.

Photographic "speed" refers to the exposure necessary to obtain a density of at least 1.0 plus $D_{min}$.

"Dynamic range" refers to the range of exposures over which useful images can be obtained.

The term "fully forehardened" is employed to indicate the forehardening of hydrophilic colloid layers to a level that limits the weight gain of a radiographic film to less than 120% of its original (dry) weight in the course of wet processing. The weight gain is almost entirely attributable to the ingestion of water during such processing.

The term "rapid access processing" is employed to indicate dry-to-dry processing of a radiographic film in 45 seconds or less. That is, 45 seconds or less elapse from the time a dry imagewise exposed radiographic film enters a wet processor until it emerges as a dry fully processed film.

In referring to grains and silver halide emulsions containing two or more halides, the halides are named in order of ascending concentrations.

The term "equivalent circular diameter" (ECD) is used to define the diameter of a circle having the same projected area as a silver halide grain.

The term "aspect ratio" is used to define the ratio of grain ECD to grain thickness.

The term "coefficient of variation" (COV) is defined as 100 times the standard deviation (a) of grain ECD divided by the mean grain ECD.

The term "covering power" is used to indicate 100 times the ratio of maximum density to developed silver measured in mg/dm².

The term "dual-coated" is used to define a radiographic film having silver halide emulsion layers disposed on both the front- and backsides of the support.

The term "RAD" is used to indicate a unit dose of absorbed radiation, that is energy absorption of 100 ergs per gram of tissue.

The term "portal" is used to indicate radiographic imaging, films and intensifying screens applied to megavoltage radiotherapy conducted through an opening or port in a radiation shield.

The term "localization" refers to portal imaging that is used to locate the port in relation to the surrounding anatomy of the irradiated subject. Typically exposure times range from 1 to 10 seconds.

The term "verification" refers to portal imaging that is used to record patient exposure through the port during radiotherapy. Typically exposure times range from 30 to 300 seconds.

The term "crossover" as herein employed refers to the percentage of light emitted by a fluorescent intensifying screen that strikes a dual-coated radiographic film and passes through its support to reach the image forming layer unit disposed on the opposite side of the support.

The terms "kVp" and "MVp" stand for peak voltage applied to an X-ray tube times $10^3$ and $10^6$, respectively.

The term "fluorescent intensifying screen" or "fluorescent screen" refers to a screen that absorbs X-radiation and emits light.

The term "metal intensifying screen" refers to a metal screen that absorbs MVp level X-radiation to release electrons and absorbs electrons that have been generated by X-radiation prior to reaching the screen.

The terms "front" and "back" refer to features or elements nearer to and farther from, respectively, the X-radiation source than the support of the radiographic element.

The term "rare earth" is used to indicate elements having an atomic number of 39 or 57 through 71.

*Research Disclosure* is published by Kenneth Mason Publications, Ltd., Dudley House, 12 North St., Emsworth, Hampshire P010 7DQ England.

The present invention is described in part by reference to the Figures.

FIG. 1 illustrates a conventional direct portal imaging receptor 10 comprising a thick (at least 1 mm) metal sheet or plate (metal intensifying screen) 12 and radiographic film 14. Radiographic film 14 can be any suitable silver halide photographic film designed for photographic imaging as described below. Examples of such films include KODAK X-Ray Therapy Localization (XTL) Film and KODAK X-ray Therapy Verification (XV) Film.

In FIG. 2, a conventional indirect portal imaging receptor 20 comprises thick (at least 1 mm) metal intensifying screen 22, front fluorescent intensifying screen 24, radiographic film 26 and back fluorescent intensifying screen 28. Metal intensifying screen 22 can be composed of any suitable metal as described below, and radiographic film 26 can be any suitable film as described herein (for example, KODAK EC Radiographic Film). The front and back fluorescent intensifying screens 24 and 28 can be any useful fluorescent intensifying screen that would be readily apparent to one skilled in the art, as described in more detail below.

The advantages of the present invention are achieved by using much thinner metal intensifying screens on the front, back or both sides of the radiographic film in the imaging assembly. The simplest arrangement is shown in FIG. 3 wherein imaging assembly 30 comprises thin (see below) metal intensifying screen 32, front fluorescent intensifying screen 34, and radiographic film 36.

Figure 3:
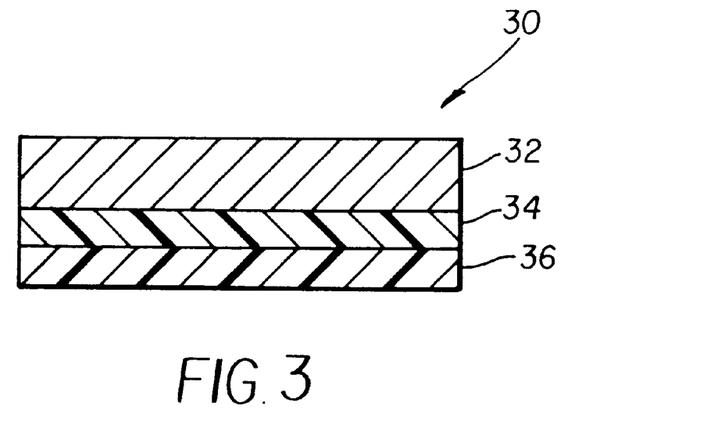
FIG. 3 is an enlarged cross sectional view of a portal imaging assembly of the present invention comprising a thin front metal intensifying screen and a front fluorescent intensifying screen with a radiographic film.
Figure 4:
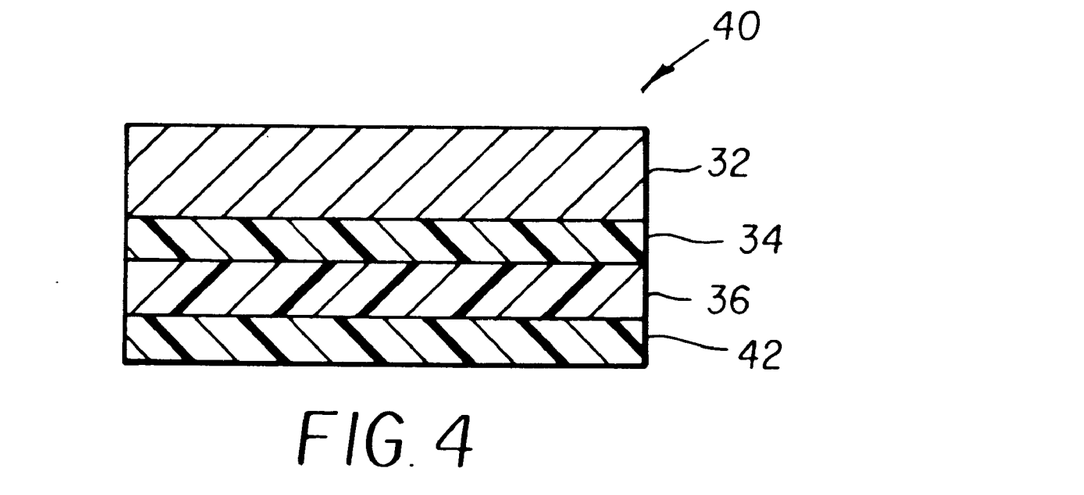
FIG. 4 is an enlarged cross sectional view of a portal imaging assembly of the present invention comprising a thin front metal intensifying screen and both front and back fluorescent intensifying screens with a radiographic film.

Another embodiment of the invention is illustrated in FIG. 4 wherein imaging assembly 40 was similar to that shown in FIG. 3 except that fluorescent intensifying screen 42 is provided on the backside.

Figure 5:
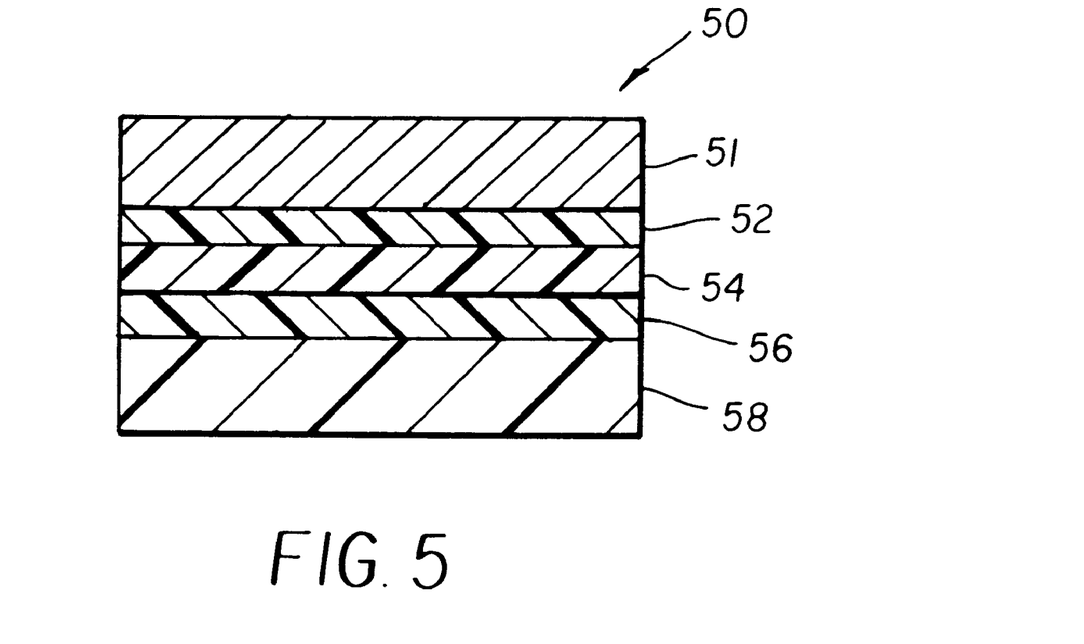
FIG. 5 is an enlarged cross sectional view of a portal imaging assembly of the present invention comprising both front and back fluorescent intensifying screens and thin front and back metal intensifying screens with a radiographic film.

In still another embodiment of the invention shown in FIG. 5, imaging assembly 50 comprises thin metal intensifying screen 51, front fluorescent intensifying screen 52, radiographic film 54, back fluorescent intensifying screen 56 and backside thin metal intensifying screen 58.

During localization portal imaging the patient is briefly exposed to 4 to 25 MVp X-radiation over a region that is somewhat larger than the radiotherapy target area for the purpose of obtaining a discernible image of anatomy reference features outside the target area. This is immediately followed by a brief exposure through the port in the shields, to create an image of the port superimposed on the broader region first exposure. Total exposure during localization imaging is limited to 10 seconds or less, typically from 1 to 10 seconds. The object is to obtain an image that confirms or guides alignment of the port for radiotherapy, but to limit exposure to the MVp X-radiation to the extent possible. By seeing in the image the location of the port in relation to reference anatomy features, the port can be more accurately aligned with the target area, if necessary, before the longer duration radiotherapy exposure begins.

If present, the metal intensifying screens each absorb Mvp X-radiation and emit electrons. The portal radiographic element itself absorbs only a very small fraction of the MVp X-radiation and the emitted electrons. The primary exposure of the portal radiographic element is provided by light emitted by the fluorescent layer of the fluorescent intensifying screens. The fluorescent layer much more efficiently than the radiographic element captures emitted electrons, resulting in light emission. The light emitted by the fluorescent intensifying screen is efficiently captured by the portal radiographic element.

Although preferred portal imaging assemblies have been described above, it is appreciated that varied imaging assembly constructions are possible.

The exact choice and number of fluorescent intensifying screens to be used during the localization and verification imaging steps can be varied, depending upon the output of the screens and the sensitivity of the portal radiographic element used in both exposures. In a specifically preferred localization imaging assembly, a back metal intensifying screen is omitted, and a second fluorescent intensifying screen is interposed between the portal radiographic element and the front metal intensifying screen. In another localization imaging assembly, two thin metal intensifying screens are employed in combination with two fluorescent intensifying screens.

To allow a single cassette construction to be employed with varied imaging assemblies, differing in functioning elements, it is conventional practice to include within the cassette a compressible foam sheet. A plastic sheet can be used, if desired, to distribute the compressive force applied by the compressible foam sheet. This allows each assembly to be similarly compressed when the cassette is closed for exposure.

The radiographic films useful in the practice of this invention have constructions that are well within the capabilities of those skilled in the art. The film can be what is known in the art as conventional "wet" chemistry processed materials.

Any conventional transparent radiographic or photographic film support can be employed in constructing the radiographic films. It is preferred to employ a radiographic film support, since this maximizes compatibility with the rapid access radiographic film processors in which the films are intended to be processed and provides a radiographic film look and feel to the processed film. Radiographic film supports usually exhibit these specific features: (1) a film support that is constructed of polyesters to maximize dimensional integrity rather than employing cellulose acetate supports as are most commonly employed in photographic elements and (2) that is blue tinted to contribute the cold (blue-black) image tone sought in the fully processed films, whereas photographic films rarely, if ever, employ blue tinted supports. Radiographic film supports, including the incorporated blue dyes that contribute to cold image tones, are described in *Research Disclosure,* Item 18431, cited above, Section XII. Film Supports. *Research Disclosure,* Vol. 365, September 1994, Item 36544, Section XV. Supports, illustrates in paragraph (2) suitable subbing layers to facilitate adhesion of hydrophilic colloids to the support. Although the types of transparent films set out in Section XV, paragraphs (4), (7) and (9) are contemplated, due to their superior dimensional stability, the transparent films preferred are polyester films, illustrated in Section XV, paragraph (8). Poly(ethylene terephthalate) and poly(ethylene naphthalene) are specifically preferred polyester film supports.

The radiographic films useful in the imaging assemblies of this invention include a flexible support having disposed on both sides thereof: one or more silver halide emulsion layers and optionally one or more non-radiation sensitive hydrophilic layer(s). The silver halide emulsions in the various layers can be the same or different, and can comprise mixtures of various silver halide emulsions in one or more of the layers.

In preferred embodiments, the film has the same silver halide emulsions on both sides of the support. It is also preferred that the films have a protective overcoat (described below) over the silver halide emulsions on each side of the support.

In the more preferred embodiments, at least one non-light sensitive hydrophilic layer is included with the one or more silver halide emulsion layers on each side of the film support. This layer may be called an interlayer or overcoat, or both.

The silver halide emulsion layers comprise one or more types of silver halide grains responsive to X-radiation. Silver halide grain compositions particularly contemplated include those having at least 50 mol % chloride (preferably at least 70 and more preferably at least 80 mol % chloride), and up to 50 mol % bromide, based on total silver in a given emulsion layer. Such emulsions include silver halide grains composed of, for example, silver chloride, silver iodochloride, silver bromochloride, silver iodobromochloride, and silver bromoiodochloride. Iodide is generally limited to no more than 3 mol % (based on total silver in the emulsion layer) to facilitate more rapid processing. Preferably iodide is from about 0.5 to about 1.5 mol % (based on total silver in the emulsion layer) or eliminated entirely from the grains. The silver halide grains in each silver halide emulsion unit (or silver halide emulsion layers) can be the same or different, or mixtures of different types of grains.

The silver halide grains useful in this invention can have any desirable morphology including, but not limited to, cubic, octahedral, tetradecahedral, rounded, spherical or other non-tabular morphologies, or be comprised of a mixture of two or more of such morphologies. Preferably, the grains in each silver halide emulsion have cubic morphology.

A variety of silver halide dopants can be used, individually and in combination, to improve contrast as well as other common properties, such as speed and reciprocity characteristics. A summary of conventional dopants to improve speed, reciprocity and other imaging characteristics is provided by *Research Disclosure,* Item 38957, cited above, Section I. Emulsion grains and their preparation, sub-section D. Grain modifying conditions and adjustments, paragraphs (3), (4), and (5). Rhodium, cadmium, lead and bismuth are all well known to increase contrast by restraining toe development. The toxicity of cadmium has precluded its continued use. Rhodium is most commonly employed to increase contrast and is specifically preferred. Contrast enhancing concentrations are known to range from as low $10^{-9}$ mole/Ag mole. A specifically preferred rhodium doping level is from $1\times10^{-6}$ to $1\times10^{-4}$ mole/Ag mole.

A variety of other dopants are known, individually and in combination, to improve not only contrast but other common properties as well, such as speed and reciprocity characteristics. Dopants capable providing shallow electron trapping sites, commonly referred to as SET dopants, are specifically contemplated. SET dopants are described in *Research Disclosure,* Vol. 367, November 1994, Item 36736. Iridium dopants are very commonly employed to decrease reciprocity failure. The extended exposure times of the portal radiographic elements render it highly desirable to include one or more dopants to guard against low intensity reciprocity failure, commonly referred to as LIRF. U.S. Pat. No. 4,997,751 (Kim), here incorporated by reference, provides a specific illustration of iridium doping to reduce LIRF. A summary of conventional dopants to improve speed, reciprocity and other imaging characteristics is provided by *Research Disclosure,* Item 36544, cited above, Section I. Emulsion grains and their preparation, sub-section D. Grain modifying conditions and adjustments, paragraphs (3), (4) and (5).

Low COV emulsions can be selected from among those prepared by conventional batch double-jet precipitation techniques. The emulsions can be prepared, for example, by incorporating a rhodium dopant during the precipitation of monodisperse emulsions of the type commonly employed in photographic reflection print elements. Specific examples of these emulsions are provided by U.S. Pat. No. 4,865,962 (Hasebe et al.), U.S. Pat. No. 5,252,454 (Suzumuto et al.), and U.S. Pat. No. 5,252,456 (Oshima et al.), the disclosures of which are here incorporated by reference. A general summary of silver halide emulsions and their preparation is provided by *Research Disclosure,* Item 36544, cited above, I. Emulsion grains and their preparation.

The emulsions can be chemically sensitized by any convenient conventional technique. Such techniques are illustrated by *Research Disclosure,* Item 36544, IV. Chemical sensitization. Sulfur or gold sensitization is specifically contemplated.

High chloride grains, particularly the specifically preferred silver bromochloride grains, possess little native sensitivity beyond the ultraviolet region of the spectrum, and are also preferably spectrally sensitized. It is specifically contemplated that one or more spectral sensitizing dyes will be absorbed to the surfaces of the grains to impart or increase their light-sensitivity. Ideally the maximum absorption of the spectral sensitizing dye is matched (for example within ±10 nm) to the principal emission band or bands of the fluorescent intensifying screen. In practice any spectral sensitizing dye can be employed which, as coated, exhibits a half peak absorption bandwidth that overlaps the principal spectral region(s) of emission by the fluorescent intensifying screen intended to be used with the portal radiographic film.

A wide variety of conventional spectral sensitizing dyes are known having absorption maxima extending throughout the near ultraviolet (300 to 400 nm), visible (400 to 700 nm) and near infrared (700 to 1000 nm) regions of the spectrum. Specific illustrations of conventional spectral sensitizing dyes is provided by *Research Disclosure,* Item 18431, Section X. Spectral Sensitization, and Item 36544, Section V. Spectral sensitization and desensitization, A. Sensitizing dyes.

Instability which increases minimum density in negative-type emulsion coatings (that is fog) can be protected against by incorporation of stabilizers, antifoggants, antikinking agents, latent-image stabilizers and similar addenda in the emulsion and contiguous layers prior to coating. Such addenda are illustrated by *Research Disclosure,* Item 36544, Section VII. Antifoggants and stabilizers, and Item 18431, Section II. Emulsion Stabilizers, Antifoggants and Antikinking Agents.

The silver halide emulsion and other layers forming the processing solution permeable imaging units on opposite sides of the support contain conventional hydrophilic colloid vehicles (peptizers and binders), typically gelatin or a gelatin derivative. Conventional vehicles and related layer features are disclosed in *Research Disclosure,* Item 36544, II. Vehicles, vehicle extenders, vehicle-like addenda and vehicle related addenda. The emulsions themselves can contain peptizers of the type set out in II above, paragraph A. Gelatin and hydrophilic colloid peptizers. The hydrophilic colloid peptizers are also useful as binders and hence are commonly present in much higher concentrations than required to perform the peptizing function alone. The vehicle extends also to materials that are not themselves useful as peptizers. Such materials are described in II above, C. Other vehicle components.

The films useful in the invention are generally fully forehardened to facilitate rapid access processing. The use of any convenient conventional hardener is contemplated. Such hardeners are described in II above, B. Hardeners.

The surface protective overcoats are typically provided for physical protection of the emulsion layers. In addition to vehicle features discussed above the overcoats can contain various addenda to modify the physical properties of the overcoats. Such addenda are illustrated by *Research Disclosure,* Item 36544, IX. Coating physical property modifying addenda, A. Coating aids, B. Plasticizers and lubricants, C. Antistats, and D. Matting agents. The interlayers are typically thin hydrophilic colloid layers that provide a separation between the emulsion and the surface overcoat addenda. It is quite common to locate some emulsion compatible types of surface overcoat addenda, such as anti-matte particles, in the interlayers.

Further details about preferred portal radiographic films useful in the practice of this invention are provided in an number of publications including U.S. Pat. No. 5,871,892 (noted above), incorporated herein by reference.

More particularly, such radiographic films comprise a film support capable of transmitting X-radiation, and one or more silver halide emulsion layers and one or more other hydrophilic colloid-containing layers, disposed on both sides thereof. The layers on each side of the support are fully forehardened and comprise a total of less than 45 mg/dm$^2$ of hydrophilic colloid(s) to facilitate processing in less than 45 seconds. Preferably, the amount of hydrophilic colloid(s) on each side of the support is from about 20 to about 45 mg/dm$^2$, and the water pick-up during rapid access processing, measured at the highest increase in element weight at any time during the processing cycle, is less than 120%. At least one of the silver halide emulsion layers on each side of the support provides a contrast in the range of from about 4 to about 8 (preferably from about 4 to about 6) and contains less than 3 mol % iodide and at least 50 mol % (based on total silver) in the silver halide grains. These films are also designed to allow at least 30% crossover within a spectral region to which the silver halide grains are sensitive. The coverage of silver on each side of the support is any conventional amount that would provide maximum densities in the range of from about 2 to about 4.

The various coated layers of radiographic films of this invention can also contain tinting dyes to modify the image tone to transmitted or reflected light. These dyes are not decolorized during processing and may be homogeneously or heterogeneously dispersed in the various layers. Preferably, such non-bleachable tinting dyes are in a silver halide emulsion layer.

A fluorescent intensifying screen can be interposed between the portal radiographic film and a front metal intensifying screen in a radiographic imaging assembly. Alternatively the fluorescent intensifying screen can be interposed between the portal radiographic film and a back metal intensifying screen. When two fluorescent intensifying screens are employed, they can be independently selected, being the same or different in composition and emission efficiencies. Each fluorescent intensifying screen is capable of giving stimulable emission at a wavelength in the range of from about 360 to about 440 nm when excited with stimulating radiation in the wavelength of from about 600 nm to about 670 nm.

The fluorescent intensifying screens useful in the present invention can take any convenient conventional form. The fluorescent (or phosphor) layers can take any of the forms of those found in intermediate to high speed fluorescent intensifying screens and typically the fluorescent intensifying screens contain a reflective or transparent film support, preferably the former. If a transparent support is employed in the imaging assembly, reflection of light from a back metal intensifying screen can be used to increase the amount of light transmitted to the portal radiographic film. If a reflective (for example, white) support is incorporated in the fluorescent intensifying screen, even a higher proportion of emitted light will reach the portal radiographic film.

Any conventional support material can be used in the fluorescent intensifying screens as described in the art mentioned in the following paragraph. Such support materials include polymer films (including polyesters and cellulose acetate) and cellulosic materials such as papers, and more particularly transparent polyester and polycarbonate films.

In some embodiments, the support materials flexible laminate support such as two more flexible substrates that are laminated or otherwise adhered together, as described in copending and commonly assigned U.S. Ser. No. 09/667,150 (filed Sep. 21, 2000 by Chen et al.).

Examples of useful fluorescent intensifying screens are provided by *Research Disclosure,* Item 18431, cited above, Section IX. X-Ray Screens/Phosphors, and U.S. Pat. No. 5,021,327 (Bunch et al.) and U.S. Pat. No. 4,994,355 (Dickerson et al.), U.S. Pat. No. 4,997,750 (Dickerson et al.), U.S. Pat. No. 5,108,881 (Dickerson et al.), and U.S. Pat. No. 5,871,892 (noted above), the disclosures of which are here incorporated by reference. The fluorescent layer contains phosphor particles and a binder, optimally additionally containing a light scattering material, such as titania. Higher emission efficiencies are realized with phosphors such as calcium tungstate ($CaWO_4$) niobium and/or rare earth activated yttrium, lutetium or gadolinium tantalates, and rare earth activated rare earth oxychalcogenides and halides.

Preferred rare earth oxychalcogenide and halide phosphors are represented by the following formula (1):

$$M'_{(w-n)}M''_nO_wX' \tag{1}$$

wherein M' is at least one of the metals yttrium (Y), lanthanum (La), gadolinium (Gd), or lutetium (Lu), M" is at least of the rare earth metals, preferably dysprosium (Dy), erbium (Er), europium (Eu), holmium (Ho), neodymium (Nd), praseodymium (Pr), samarium (Sm), terbium (Tb), thulium (Tm), or ytterbium (Yb), X' is a middle chalcogen (S, Se or Te) or halogen, n is 0.002 to 0.2, and w is 1 when X' is halogen or 2 when X is chalcogen.

One useful phosphor layer is composed of $Gd_2O_2S:Tb$ in a suitable binder.

Other examples of suitable phosphors also include the various classes of materials described in U.S. Pat. No. 4,835,397 (Arakawa et al.) and U.S. Pat. No. 5,381,015 (Dooms), both incorporated herein by reference, and including for example divalent europium and other rare earth activated alkaline earth metal halide phosphors and rare earth element activated rare earth oxyhalide phosphors. Of these types of phosphors, the more preferred phosphors include alkaline earth metal fluorohalide storage phosphors [particularly those containing iodide such as alkaline earth metal fluorobromoiodide storage phosphors as described in U.S. Pat. No. 5,464,568 (Bringley et al.)].

The phosphor layer(s) can comprise one or more phosphors that contain iodide in one or more of those layers. In particular, the alkaline earth metal phosphors can be the products of firing starting materials comprising optional oxide and a combination of species characterized by the following formula (2):

$$MFX_{1-z}I_zuM^aX^a:yA:eQ:tD \tag{2}$$

wherein "M" is magnesium (Mg), calcium (Ca), strontium (Sr) or barium (Ba), "F" is fluoride, "X" is chloride (Cl) or bromide (Br), "I" is iodide, $M^a$ is sodium (Na), potassium (K), rubidium (Rb) or cesium (Cs), $X^a$ is fluoride (F), chloride (Cl), bromide (Br) and iodide (I), "A" is europium (Eu), cerium (Ce), samarium (Sm) or terbium (Tb), "Q" is $BeO$, $MgO$, $CaO$, $SrO$, $BaO$, $ZnO$, $Al_2O_3$, $La_2O_3$, $In_2O_3$, $SiO_2$, $TiO_2$, $ZrO_2$, $GeO_2$, $SnO_2$, $Nb_2O_5$, $Ta_2O_5$, or $ThO_2$, "D" is vanadium (V), chromium (Cr), manganese (Mn), iron (Fe), cobalt (Co) or nickel (Ni). The numbers in the noted formula are the following: "z" is $1 \times 10^{-4}$ to 1, "u" is from 0 to 1, "y" is from $1 \times 10^{-4}$ to 0.1, "e" is form 0 to 1, and "t" is from 0 to 0.01. These definitions apply wherever they are found in this application unless specifically stated to the contrary. It is also contemplated that "M", "X", "A" and "D" represent multiple elements in the groups identified above.

In some embodiments, the divalent alkaline earth metal fluorohalide phosphors containing iodide are the product of firing an intermediate, comprising oxide and a combination of species characterized by the following formula (3):

$$(Ba_{1-a-b-c}Mg_aCa_bSr_c)FX_{1-z}I_zrM^aX^a:yA \tag{3}$$

wherein X, $M^a$, $X^a$, A, z and y have the same meanings as for formula (1) and the sum of a, b and c is from 0 to 4, and r is from $10^{-6}$ to 0.1. Some embodiments of these phosphors are described in more detail in U.S. Pat. No. 5,464,568 (noted above), incorporated herein by reference.

In another embodiment, the phosphor be a storage phosphor produced utilizing an oxosulfur reducing agent containing phosphor intermediate as described in U.S. Pat. No. 5,427,868 (noted above), incorporated herein by reference.

Examples of other phosphors employable in the radiation image storage panel include: SrS:Ce,SM, SrS:Eu,Sm, ThO2:Er, La2O2S:Eu,Sm, ZnS:Cu,Pb, and others described in U.S. Pat. No. 5,227,253 (noted above).

The phosphors useful herein can be provided as particulate materials disposed within the binder, or in the form of particles encapsulated with a polymeric material (like a core-shell arrangement). Various polymeric shell materials include polyesters, nitrocellulose, polyalkyl acrylates and methacrylates, as well as vinyl epoxy resins described in U.S. Pat. No. 5,646,412 (Bryan et al.). A coupling agent can be used to facilitate the formation of the polymer shell directly onto the surface of the phosphor particles and to provide good adhesion between the two components.

A mixture of phosphors can be used, and particularly a mixture of phosphors containing iodide is useful. If more than one storage phosphor layers are used, those layers can be composed of the same or different storage phosphors and the same or different binders. The multiple phosphor layers can also have the same or different thickness. The amount of the one or more phosphors in the phosphor layers is generally at least 50 weight percent, and preferably from about 80 to about 98 weight percent, based on total dry layer weight.

The phosphor layers comprise one or more binders to give the layers structural coherence. In general, the binders useful in this invention are those conventionally used for this purpose in the art. They can be chosen from a wide variety of known organic polymers that are transparent to X-radiation, stimulating and emitted radiation. Binder materials commonly used for this purpose include but are not limited to, natural polymers such as proteins (for example gelatins), polysaccharides (such as dextrans), poly(vinyl acetate), ethyl cellulose, vinylidene chloride polymers, cellulose acetate butyrate, polyvinyl alcohol, sodium o-sulfobenzaldehyde acetal of poly(vinyl alcohol), chlorosulfonated poly(ethylene), a mixture of macromolecular bisphenol poly(carbonates), and copolymers comprising bisphenol carbonates and poly(alkylene oxides), aqueous ethanol soluble nylons, poly(alkyl acrylates and methacrylates) and copolymers of poly(alkyl acrylates and methacrylates and acrylic acid or methacrylic acid) and poly(vinyl butryal) and poly(urethanes) elastomers. Mixtures of binders can be used if desired. These and other useful binder materials are described in U.S. Pat. No. 2,502,529 (Luckey), U.S. Pat. No. 2,887,379 (Ralph et al.), U.S. Pat. No. 3,617,285 (Staudenmeyer), U.S. Pat. No. 3,300,310 (Kenneth et al.), U.S. Pat. No. 3,300,311 (Kenneth et al.), U.S. Pat. No. 3,743,833 (Martic et al.), U.S. Pat. No. 4,574,195 (Teraoka et al.), and in *Research Disclosure* Vol. 154, February 1977, publication 15444 and Vol. 182, June 1979.

Particularly useful binders are polyurethanes such as those commercially available as ESTANE polyurethanes from Goodrich Chemical Co., PERMUTHANE polyurethanes from Permuthane Division of ICI.

The binder(s) are present in the phosphor layers in an amount of at least 3 weight percent, and preferable from about 5 to about 12.5 weight percent, based on total phosphor dry weight.

Any conventional ratio of phosphor to binder can be used in the imaging assemblies of this invention. Generally thinner phosphor layers and sharper images are obtained when a high weight ratio of phosphor to binder is used. Preferably phosphor to binder weight ratios are in the range of from about 7:1 to about 30:1. More or less binder can be used if desired for specific applications.

The one or more phosphor layers can include other addenda that are commonly employed for various purposes, including but not limited to reducing agents (such as oxysulfur reducing agents), phosphites and organotin compounds to prevent yellowing, dyes and pigments for light absorption, plasticizers, dispersing aids, surfactants, and antistatic agents, all in conventional amounts.

The one or more phosphor layers generally have a total dry thickness of at least 50 $\mu$m, and preferably from about 100 $\mu$m to about 400 $\mu$m.

The fluorescent screens preferably include a protective overcoat layer disposed on the one or more phosphor layers. This layer is substantially clear and transparent to the light emitted by the phosphor and provides abrasion and scratch resistance and durability. It may also be desirable for the overcoat layer to provide a barrier to water or water vapor that may degrade the performance of the phosphor. Further, it may be desirable to incorporate components into the overcoat layer that prevent yellowing of the storage panel.

Many such materials are known in the art, including but not limited to, polyesters [such as poly(ethylene terephthalate)], polyethylene, polyamides, poly(vinyl butyral), poly(vinyl formal), polycarbonates, vinyl chloride polymers, acrylic polymers [such as poly(methyl methacrylate) and poly(ethyl methacrylate)], and various polymer blends of fluorinated polymers and non-fluorinated polymers [such as blends of polyacrylates and vinylidene fluoride polymers. Mixtures of materials can be used if desirable. Other useful overcoat materials are described in U.S. Pat. No. 4,574,195 (Teraoka et al.), U.S. Pat. No. 5,401,971 (Roberts), U.S. Pat. No. 5,227,253 (Takasu et al.), U.S. Pat. No. 5,475,229 (Itabashi et al.), all incorporated herein by reference. The preferred materials are poly (vinylidene fluoride-co-tetrafluoroethylene), poly (vinylidene fluoride-co-chlorotrifluoroethylene), and blends of poly(vinylidene fluoride-co-tetrafluoroethylene) and poly [($C_{1-2}$ alkyl)methacrylate].

The protective overcoat may also be formed through the use of radiation curable compositions as those described in U.S. Pat. No. 5,149,592 (Wojnarowicz).

In addition to the film-forming polymer, the overcoat may contain a variety of agents designed to enhance its utility. Such agents include solid particulate materials or mattes as described in U.S. Pat. No. 4,059,768 (VanLandeghem et al.) and antistatic agents as described in U.S. Pat. No. 5,569,485 (Dahlquist et al.).

The protective overcoat layer can extend over the storage panel to seal the edges of the phosphor layer(s) or a separate seal may be applied using the same composition as that of the overcoat or a different composition.

While anticurl layers are not required for the fluorescent screens, they are generally preferred in order to balance the forces exerted by the coating of the phosphor layer(s) and protective overcoat. Materials used to form anticurl layers include those identified above for use as binder materials or overcoat layer materials.

Subbing layers may be disposed between the support and the phosphor layer(s) is desired to enhance layer adhesion. Materials useful for this purpose are those conventionally used in subbing layers in photographic silver halide materials and are described for example in *Research Disclosure* Vole. 176, December 1978, publication 17643 (Section XVII) and Vol. 184, August 1979, publication 18431 (Section I).

The metal intensifying screens useful in this invention can take any convenient conventional form. While metal intensifying screens are most easily fabricated as thin foils, they are often mounted on radiation transparent backings to facilitate handling. Convenient metals for screen fabrication are in the atomic number range of from 22 (titanium) to 82 (lead). Metals such as copper, lead, tungsten, iron and tantalum have been most commonly used for metal intensifying screen fabrication with lead and copper in that order being the most commonly employed metals.

The metal intensifying screens used in practice of this invention are thinner than conventional screens. They typically range from about 0.05 to 0.75 mm in thickness particularly when employed as a front screen. A preferred front screen thickness range for lead is from about 0.1 to 0.75 mm for copper and from about 0.05 to about 0.4 mm for lead. Preferably, the thickness is from about 0.1 to about 0.6 mm for copper screens and from about 0.05 to about 0.3 mm for lead screens. Most preferred copper screens have a thickness of from about 0.1 to about 0.5 mm.

If used, back metal intensifying screens can be constructed of the same materials as the front metal intensifying screens and can have the same or different thickness. Preferably, the back metal intensifying screens also have a thickness within the ranges noted above.

Instead of employing separate metal and fluorescent intensifying screens, it is possible to integrate both functions into a single element by coating a fluorescent layer onto one or both of the metal intensifying screens. Those metal screens would have the thickness within the ranges described above.

The imaging assemblies described herein can be packaged and/or used in a light-tight imaging article similar to those described for example in U.S. Pat. No. 5,871,892 (noted above, for example in Column 5). A commercial container of this type is available as KODAK EC-L System.

Processing of the radiographic films of this invention can be undertaken in any convenient conventional manner. The processing techniques of U.S. Pat. Nos. 5,021,327 and 5,576,156 (both noted above), are typical for processing radiographic films. Other processing compositions (both developing and fixing compositions) are described in U.S. Pat. No. 5,738,979 (Fitterman et al.), U.S. Pat. No. 5,866,309 (Fitterman et al.), U.S. Pat. No. 5,871,890 (Fitterman et al.), U.S. Pat. No. 5,935,770 (Fitterman et al.), U.S. Pat. No. 5,942,378 (Fitterman et al.), all incorporated herein by reference. The processing compositions can be supplied as single- or multi-part formulations, and in concentrated form or as more diluted working strength solutions.

It is particularly desirable that the films be processed within 90 seconds ("dry-to-dry"), and preferably within 45 seconds and at least 20 seconds, including developing, fixing and any washing (or rinsing). Such processing can be carried out in any suitable processing equipment including but not limited to, a Kodak X-OMAT™ RA 480 processor that can utilize Kodak Rapid Access processing chemistry. Other "rapid access processors" are described for example in U.S. Pat. No. 3,545,971 (Barnes et al.) and EP-A-0 248,390 (Akio et al.).

The "wet" chemistry processed radiographic films described above for use in the imaging assemblies can be processed to provide an image using conventional black-and-white processing compositions (that is developing and fixing compositions). Representative developing and fixing compositions include KODAK RP Developer and KODAK RP Fixer (both from Eastman Kodak Company). Processing conditions are also well known in the art.

In practicing the therapy imaging method of this invention, X-radiation, typically of from about 4 to about 25 MVp, is directed at a region of the subject (that is, patient) containing features to be identified by different levels of X-radiation absorption. This exposed region is generally somewhat larger than the radiotherapy target area for the purpose of obtaining a discernible image of anatomy reference features outside the targeted area. Thus, a first image is created in the radiographic film as the X-radiation penetrates the subject.

A shield containing a port is generally placed between the subject and the source of X-radiation, and X-radiation is again directed at the subject, this time through the portal, thereby creating a second image through the port that is superimposed on the first image in the radiographic film. The total exposure during these steps A and B for localization imaging is generally limited to 10 seconds or less.

The following examples are illustrative of the present invention but the invention is not meant to be so limited.

EXAMPLE 1

Imaging Assembly

Imaging assemblies (cassettes) were constructed with pairs of KODAK LANEX Fast fluorescent intensifying screens and a series of 5 cm×5 cm pieces of copper sheets varying from 0.1 to 0.8 mm in thickness placed in front of the front fluorescent intensifying screens. Using a conventional Varian, Inc. radiation therapy treatment machine, a 15-cm plastic patient tissue phantom was exposed using 6 Mvx through each imaging assembly. We were surprised to observe that the optical densities behind each of the different copper screens were within 0.08. This is an indication that desired photospeed could be obtained even with thinner copper metal screens.

EXAMPLE 2

Radiographic Imaging Assembly

Radiographic imaging assemblies (cassettes) were constructed with pairs of KODAK LANEX Fast fluorescent intensifying screens and a series of 12.7 cm×12.7 cm pieces of copper sheets varying from 0.1 to 0.8 mm in thickness placed in front of the front fluorescent intensifying screens. Behind the fluorescent screens was placed a sample of KODAK EC Radiographic Film.

A similar radiographic imaging assembly was constructed without a metal screen and used as a Control imaging assembly. A second control was a conventional KODAK EC-L Cassette (imaging assembly).

A piece of Lucite plastic (15.25 cm thick) was placed in front of a wooden film holder to simulate a patient.

All of the imaging assemblies were exposed to a conventional $Co^{60}$ (1.2 MeV) source to the same dose. We observed that all of the imaging assemblies of this invention having copper screens with a thickness less than 0.8 mm provided optical densities within 0.1 of each other. This is an indication that desired photospeed could be obtained even with thinner copper metal screens.

EXAMPLE 3

Radiographic Imaging Assemblies

Example 2 was repeated using radiographic imaging assemblies constructed from cardboard. The results from imaging were identical.

EXAMPLE 4

A "contrast-detail" phantom was constructed from an aluminum plate (1.25 cm thick) having rows of flat bottom holes drilled to different depths and with different diameters. Such phantom constructions are well known in the art, and it also known that the imaging signals obtained using such a phantom are proportional to the volume of the drilled holes.

This phantom was used with the experimental imaging protocol described in Example 2. A piece of Lucite plastic (7.6 cm thick) was placed in front of the phantom and another was placed in back of it. The resulting imaged films were evaluated.

The current KODAK EC-L cassette (imaging assembly), comprising a 1-mm front copper metal screen, provided excellent results. However, it was surprising to us that the quality of the image was diminished only a little when the thickness of the front copper screen was reduced to as thin as 0.1 mm in the imaging assemblies. There was a significant drop in image quality when no front copper screen was used in the imaging assembly. This is evidence that the front metal screen thickness can be reduced significantly without a significant degradation in image quality.

EXAMPLE 5

Full-size imaging assemblies (cassettes, 35 cm×43 cm) were constructed using front copper screens of 0.25 mm, 0.5 mm and 0.75 mm thickness in front of KODAK LANEX fluorescent intensifying screens.

The contrast-detail phantom described in Example 4 was exposed in combination with a phantom consisting of 15 cm of tissue-equivalent plastic, through these imaging assemblies using a commercial radiation therapy treatment machine (Varian, Inc.) at 6MVx and 12MVx. A 10-cm square field was used. Surprisingly, the image quality was measured at Co (60) energies to be almost as good the image obtained using the commercial imaging assembly. Thus, the front metal screens can be reduced in thickness considerably without significant loss in imaging quality.

EXAMPLE 6

A larger contrast detail phantom (25.4 cm square) was constructed in similar fashion as described in Example 4. Imaging assemblies like those described in Example 5 were used with this phantom and 10-cm and 22-cm square fields to simulate the effect of larger treatment fields. We again found that the use of thinner front metal screens did not significantly diminish image quality.

The invention has been described in detail with particular reference to preferred embodiments thereof, but it will be understood that variations and modifications can be effected within the spirit and scope of the invention.

We claim:

1. An imaging assembly comprising a metal intensifying screen that is positioned adjacent to a fluorescent intensifying screen, said metal intensifying screen having a thickness of from about 0.1 to 0.75 mm when composed of copper or a thickness of from about 0.05 to 0.40 mm when composed of lead.

2. A radiographic imaging assembly comprising a dual emulsion-coated radiographic silver halide film provided in combination with a metal intensifying screen that is positioned adjacent to the frontside of said radiographic film, and a fluorescent intensifying screen that is interposed between said radiographic silver halide film and said metal intensifying screen, said metal intensifying screen having a thickness of from about 0.1 to 0.75 mm when composed of copper or a thickness of from about 0.05 to 0.40 mm when composed of lead.

3. The radiographic imaging assembly of claim 2 wherein said metal intensifying screen has a thickness of from about 0.1 to about 0.60 mm when composed of copper.

4. The radiographic imaging assembly of claim 3 wherein said metal intensifying screen has a thickness of from about 0.1 to about 0.50 mm when composed of copper.

5. The radiographic imaging assembly of claim 2 wherein said metal intensifying screen has a thickness of from about 0.1 to about 0.30 when composed of lead.

6. The radiographic imaging assembly of claim 2 further comprising a second fluorescent intensifying screen positioned adjacent the backside of said radiographic film.

7. The radiographic imaging assembly of claim 6 further comprising a second metal intensifying screen positioned adjacent the backside of said radiographic silver halide film so that said second fluorescent intensifying screen is interposed between said radiographic silver halide film and said second metal intensifying screen.

8. The radiographic imaging assembly of claim 2 wherein said radiographic silver halide film comprises a support having first and second major surfaces and that is capable of transmitting X-radiation, the film having disposed on the first major support surface, one or more hydrophilic colloid layers including a silver halide emulsion layer, and on the second major support surface, one or more hydrophilic colloid layers including a silver halide emulsion layer, each of the silver halide emulsion layers comprising silver halide grains that (a) have the same or different composition in each silver halide emulsion layer, and (b) are composed of at least 50 mol % chloride and up to 3 mol % iodide, based on total silver, and all hydrophilic layers of the film being fully forehardened and wet processing solution permeable for image formation within 45 seconds.

9. The radiographic imaging assembly of claim 8 wherein the amount of hydrophilic colloid(s) on each side of the support of said radiographic film is from about 20 to about 45 mg/dm$^2$, and at least one of the silver halide emulsion layers on each side of the support provides a contrast in the range of from about 4 to about 8.

10. The radiographic imaging assembly of claim 2 wherein said fluorescent intensifying screen comprises a support having therein a phosphor layer that is capable of giving stimulable emission at a wavelength in the range of from about 360 nm to about 440 nm when excited with stimulating radiation in the wavelength range of from about 600 nm to about 670 nm.

11. The radiographic imaging assembly of claim 10 wherein said phosphor layer comprises a binder having dispersed therein a rare earth activated alkaline earth metal halide phosphor or rare earth element activated rare earth oxyhalide phosphor.

12. The radiographic imaging assembly of claim 10 wherein said phosphor is a rare earth oxychalcogenide and halide phosphor represented by the following formula (1):

$$M'_{(w-n)}M''_nO_wX' \qquad (1)$$

wherein M' is at least one of the metals yttrium (Y), lanthanum (La), gadolinium (Gd), or lutetium (Lm), M" is at least of the rare earth metals, preferably dysprosium (Dy), erbium (Er), europium (Eu), holmium (Ho), neodymium (Nd), praseodymium (Pr), samarium (Sm), terbium (Tb), thulium (Tm), or ytterbium (Yb), X' is a middle chalcogen (S, Se or Te) or halogen, n is 0.002 to 0.2, and w is 1 when X' is halogen or 2 when X is chalcogen.

13. The radiographic imaging assembly of claim 10 wherein said phosphor layer comprises one or more phosphors that contain iodide, and is the product of firing starting materials comprising optional oxide and a combination of species characterized by the following formula (2):

$$MFX_{1-z}I_zuM^aX^a:yA: eQ:tD \qquad (2)$$

wherein "M" is magnesium (Mg), calcium (Ca), strontium (Sr) or barium (Ba), "F" is fluoride, "X" is chloride (Cl) or bromide (Br), "I" is iodide, $M^a$ is sodium (Na), potassium (K), rubidium (Rb) or cesium (Cs), $X^a$ is fluoride (F), chloride (Cl), bromide (Br) and iodide (1), "A" is europium (Eu), cerium (Ce), samarium (Sm) or terbium (Tb), "Q" is BeO, MgO, CaO, SrO, BaO, ZnO, Al$_2$O$_3$, La$_2$O$_3$, In$_2$O$_3$, SiO$_2$, TiO$_2$, ZrO$_2$, GeO$_2$, SnO$_2$, Nb$_2$O$_5$, Ta$_2$O$_5$, or ThO$_2$, "D" is vanadium (V), chromium (Cr), manganese (Mn), iron (Fe), cobalt (Co) or nickel (Ni), "z" is 1×10$^{-4}$ to 1, "u" is from 0 to 1, "y" is from 1×10$^{-4}$ to 0.1, "e" is form 0 to 1, and "t" is from 0 to 0.01.

14. The radiographic imaging assembly of claim 10 wherein said phosphor layer comprises one or more phosphors that contain iodide and is a divalent alkaline earth metal fluorohalide phosphors characterized by the following formula (3):

$$(Ba_{1-a-b-c}Mg_aCa_bSr_c)FX_{1-z}I_zrM^aX^a:yA \qquad (3)$$

wherein "M" is magnesium (Mg), calcium (Ca), strontium (Sr) or barium (Ba), "F" is fluoride, "X" is chloride (Cl) or bromide (Br), "I" is iodide, $M^a$ is sodium (Na), potassium (K), rubidium (Rb) or cesium (Cs), $X^a$ is fluoride (F), chloride (Cl), bromide (Br) and iodide (I), "A" is europium (Eu), cerium (Ce), samarium (Sm) or terbium (Tb), "z" is $1 \times 10^{-4}$ to 1, "y" is from $1 \times 10^{-4}$ to 0.1, the sum of a, b and c is from 0 to 4, and r is from $10^{-6}$ to 0.1.

15. The radiographic imaging assembly of claim 10 wherein said phosphor layer comprising as a phosphor, SrS:Ce,SM, SrS:Eu,Sm, $ThO_2$:Er, $La_2O_2S$:Eu,Sm, or ZnS:Cu,Pb.

16. The radiographic imaging assembly of claim 2 wherein said fluorescent intensifying screen comprises a flexible laminate support.

17. A radiographic imaging assembly useful for portal imaging comprising a dual emulsion-coated radiographic silver halide film provided in combination with a copper metal intensifying screen that is positioned adjacent to the frontside of said radiographic film, and a fluorescent intensifying screen that is interposed between said radiographic silver halide film and said copper intensifying screen, said copper intensifying screen having a thickness of from about 0.1 to about 0.4 mm, said fluorescent intensifying screen comprising a phosphor layer comprising $Gd_2O_2S$:Tb dispersed in a binder.

18. The imaging assembly of claim 17 further comprising a second fluorescent intensifying screen adjacent the backside of said radiographic silver bromide film.

19. A method of confirming the targeting of X-radiation comprising:
   A) positioning the radiographic imaging assembly of claim 2 to a region of a subject,
   B) directing the X-radiation at said region of said subject containing features that are identifiable by differing levels of X-radiation absorption and creating a first image of X-radiation penetrating said subject in the radiographic film as part of said radiographic imaging assembly,
   C) directing X-radiation at said region of said subject and creating a second image superimposed on said first image in said radiographic film,
   D) processing said radiographic film to obtain a viewable image from which intended targeting of the X-radiation directed at said region in relation to identifiable features of said subject is realized,
   wherein during steps A and B, total X-radiation exposure is limited to 10 seconds or less.

* * * * *